United States Patent [19]

Wüstenberg et al.

[11] 4,137,779
[45] Feb. 6, 1979

[54] METHODS AND ARRANGEMENT FOR THE DETERMINATION OF CRACK-DEPTHS IN ULTRASONIC NON DESTRUCTIVE TESTING

[75] Inventors: Hermann Wüstenberg; Eduard Schulz, both of Berlin, Fed. Rep. of Germany

[73] Assignee: Kraftwerk Union Aktiengesellschaft, Mülheim, Fed. Rep. of Germany

[21] Appl. No.: 422,875

[22] Filed: Dec. 7, 1973

[30] Foreign Application Priority Data

Dec. 8, 1972 [DE] Fed. Rep. of Germany ....... 2260932

[51] Int. Cl.² .............................................. G01N 29/04
[52] U.S. Cl. ......................................... 73/627; 73/628
[58] Field of Search .................. 73/67.7, 67.6, 67.5 R, 73/71.5 US, 67.8 R, 67.8 S, 627, 628, 644

[56] References Cited

U.S. PATENT DOCUMENTS

| | | | |
|---|---|---|---|
| 2,628,335 | 2/1953 | Drake | 73/625 |
| 2,799,157 | 7/1957 | Pohlman | 73/624 |
| 2,912,854 | 11/1959 | Schubring | 73/644 |
| 2,995,925 | 8/1961 | Worlton | 73/627 |
| 3,332,278 | 7/1967 | Wood et al. | 73/628 |
| 3,572,099 | 3/1971 | Wieczorek | 73/602 |
| 3,592,052 | 7/1971 | Giacomo | 73/620 |
| 3,608,352 | 9/1971 | Walton | 73/628 |
| 3,687,219 | 8/1972 | Langlois | 73/644 |

*Primary Examiner*—Stephen A. Kreitman
*Attorney, Agent, or Firm*—Herbert L. Lerner

[57] ABSTRACT

A method of determining depth propagation of a defect in a body by ultrasonic materials testing wherein a first angle probe having an ultrasonic wave transmitting oscillator produces a scatter signal at structural inhomogeneities of a body formed with a defect and the scatter signal is received by an ultrasonic wave receiving oscillator of a second angle probe, which includes: transmitting an ultrasonic wave at a first angle along a first line in direction towards the defect so that the scatter signal thereat is shadowed by the defect and diminished in intensity; receiving the diminished signal from the defect at a second angle in a direction along a second line intersecting with the first line at a defect, transmitting additional ultrasonic waves and receiving diminished scatter signals along respective lines intersecting at the defect at varying depths of the body and ascertaining the depth propagation of the defect by a marked increase in intensity of the received signal when the intersection of the respective lines along which the ultrasonic wave is transmitted and the scatter signal is received reach beyond the innermost limit of the defect.

4 Claims, 6 Drawing Figures

METHODS AND ARRANGEMENT FOR THE DETERMINATION OF CRACK-DEPTHS IN ULTRASONIC NON DESTRUCTIVE TESTING

The invention concerns a technique for determining the depth of defects near the surface of a workpiece. The technique utilizes the fact that a defect prevents the propagation from an angle probe of ultrasonic waves scattered in the structure.

There exist a number of methods for determining the depth of a defect by ultrasonic waves. However, none of these methods produce sufficient accuracy when measuring from the surface of a workpiece the depth of a defect located in the vicinity of the surface and, for example, oriented perpendicular to it. This is usually the case in materials testing, since defects frequently occur near the surface or originate from there. Although it is possible to demonstrate such defects with suitable probes by the ultrasonic pulse-echo method, such as using transversal or longitudinal waves which are propagated at a small angle relative to the surface, or also surface waves, the signals indicated, such as the echo height or stationary, do not provide any accurate information on the depth of the defect. In the case of machined surfaces, only defects of a depth in the order of up to 5 mm can be ascertained from the echo height. If the defect is deeper, no proportionality can be expected.

The object of the present invention is therefore to find a method which permits measurements proportional to the depth of defect to be made for defects which run even deeper, e.g. down to 30–40 mm. This was achieved by an angle probe producing an obliquely incident longitudinal wave beam creating scatter waves in the structure which are received by a second angle probe designed as a directional receiver for ultrasonic waves, to provide a maximum signal on a defect situated between both angle probes at a position depending on the depth of the defect.

Instead of two angle probes of variable distance relative to each other, this arrangement may be modified by using two angle probes with a bank of several oscillators (usually piezo-ceramic elements) which are electrically switched as desired to reflect a position change.

A further possible arrangement involves the use of specially-focusing (e.g. line or dot focus) angle probes or oscillator devices to obtain a more accurate resolution for determining the depth of a defect.

Another feature of the invention is the use of angle probes which emit and receive longitudinal waves to avoid disturbing surface waves.

A variation in the arrangement of the method is the placing of an angle probe on both sides of a defect on the surface where a defect has been established by other means. One of the angle probes operates as transmitter, the other as receiver. The height of the first signal (a longitudinal wave, if surface waves have been eliminated) following the transmitting pulse is picked up by the receiver and recorded. The beam angles of both angle probes are equal, as is the distance of either probe to the defect. The angle probes are moved in a manner maintaining an equidistant position of each angle probe to the defect throughout every phase of the movement. During the movement of the angle probes, the probe acting as receiver records the height of the signal which consists of longitudinal waves scattered by the structure. Since a defect, if deep enough, shades the ultrasonic beam of the emitting probe where the probes are arranged at short distances from the defect, the receiving probe cannot receive any signals at a greater height from the structure. Only when the maximum-intensity line of the sound beam of the emitting probe reaches the lower limit of the defect, will there be a marked rise in the height of the signal received from the structure. Thus the pattern of the signal height above the distance of the probes from the defect identifies the depth of the defect.

In yet another arrangement, the movement of the angle probes may be replaced by several smaller probes arranged at an increasing distance from the defect, or by several piezo-electric oscillating elements on a plastic support, where the transmitter and the receiver combinations are switched on successively to simulate the movement of the angle probes.

A further variation of the method is the arrangement of two probes fixed equidistant from the crack and on both sides of it. By changing the angle of the oscillators in the probe, longitudinal waves of differing angle of incidence are produced in the workpiece to scan the depth of the defect. Only when the lowermost limit of the defect is reached will the receiving probe indicate noise signals from the structure.

Another possible arrangement is one in which a probe is fixed on one side of the defect, and this may be a compressional wave probe for receiving longitudinal waves scattered perpendicular to the surface, while the second probe on the other side of the defect is an angle probe for obliquely incident longitudinal waves. The second probe is either changed with regard to its angle of incidence or its position to the defect, or replaced by several oscillators at different distances to the defect.

The particular advantage of the invention lies in the fact that, due to scattering at the structure, the depth of a defect can be determined from the surface of a workpiece without serious disturbances caused by coupling variations and other parameters which affect the absolute echo height in normal ultrasonic pulse-echo methods and which tend to vary greatly. This applies regardless of whether the defect runs to the surface or not.

The invention is explained in detail in the following drawings showing different arrangements.

In FIG. 1, two angle probes are arranged on both sides of the defect to produce and receive longitudinal wave beams at the same oblique angle of incidence relative to the normal at the surface.

Figure 5:
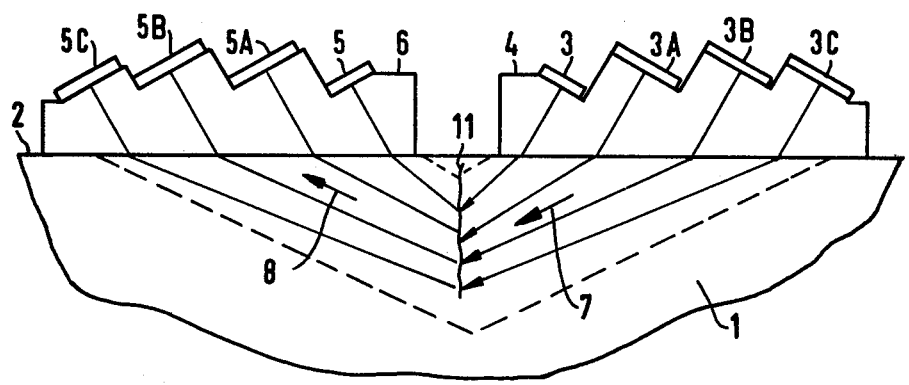

FIG. 5 involves an arrangement in which a probe provided with several oscillators is positioned on either side of the defect.

Figure 1:
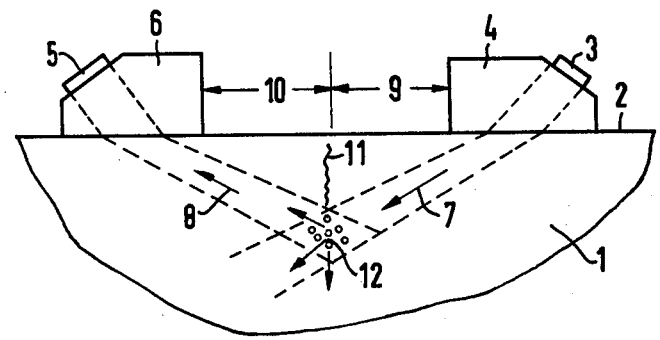
Figure 2:
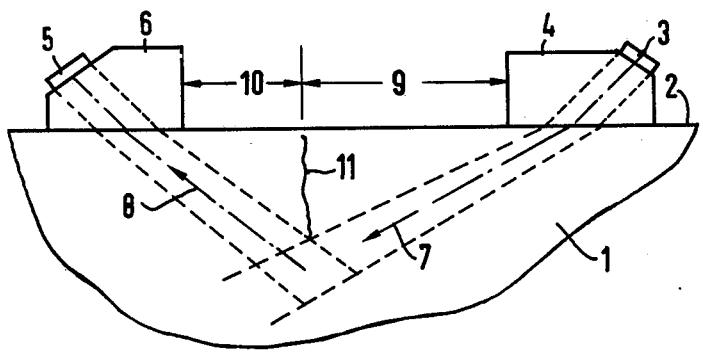
FIG. 2 shows the same arrangement as FIG. 1, but with the waves of both probes incident at a different angle.
Figure 6:
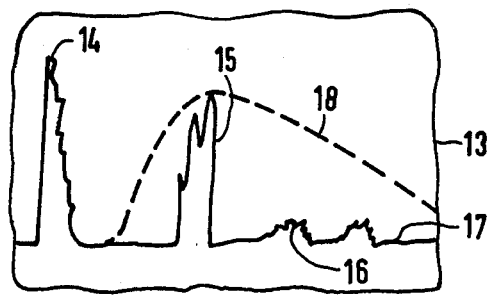

FIG. 6 gives a typical oscillogram for an arrangement according to FIG. 1 or FIG. 2 if the probes in FIG. 1 or FIG. 2 are moved away from the defect in uniform movement.

Details concerning the features of the invention are described in the illustrations.

The two angle probes with the transmitting oscillator 3 and the receiving oscillator 5 are shown in FIG. 1. The longitudinal wave beam 7 produced by probe 4 excites a limited volume and creates scatter waves in it at the structural inhomogeneities 12 which are received by the directionally receiving probe 6 with the imaginary wave beam 8 from the limited volume outlined. The structure of the workpiece 1 with the surface 2 has to be taken into account insofar as relatively clear signals may initially be expected where the grain is coarse, but which become fainter again if a grain even coarser than the former is encountered, since the receiving wave 8 also scatters at the structure. By selecting the working frequency of the ultrasonic pulse (e.g. 2 or 4MHz) generated by oscillator 3, it is possible to adjust the frequency to the workpiece and its structure as the individual case may require. For example, the workpiece may consist of a combination of ferritic base metal and an austenitic cladding applied to the surface area. With regard to frequency, the same applies to the arrangements shown in FIG. 2, 3, 4 and 5.

By selecting suitably shaped oscillators, the sound field of the transmitting probe (beam 7 in FIG. 1) and the receiving probe (beam 8 in FIG. 1) can be made to form a line focus or dot focus in the area where the two wave beams intersect. If the defect 11 is situated in the centre of the intersection area, probe 6 will only receive very weak scatter signals. The intensity of the scatter signals received by probe 6 will increase only when, by equidistant separation of the probes from the defect, the distances 9 and 10 between the probes and the defect projection to the surface have increased to the point where both sound beams intersect below the defect.

The oscillogram 13 of an ultrasonic pulse-echo device shows the resulting echo envelope curve 18 indicated as a dotted line in FIG. 6, in addition to the transmission pulse 14, the received longitudinal wave pulse 15 of the scatter signals, parasitic surface waves and transverse waves 16 and the zero line 17 of the trace on the cathode-ray tube. In suitable test blocks, the location of the steep rise of envelope curve 18 can be found as a function of the depth of artificial defects. With the aid of a calibration curve found in this manner, the depth of defects in workpieces can be very closely determined.

FIG. 2 shows an arrangement similar to that in FIG. 1, but with different angles of the sound beams at the transmitting and receiving probe. This arrangement permits the method to be applied even where the existing geometry is unfavourable if, for example, the space available on one side of the defect location is insufficient to allow the necessary movement of the probe.

Figure 3:
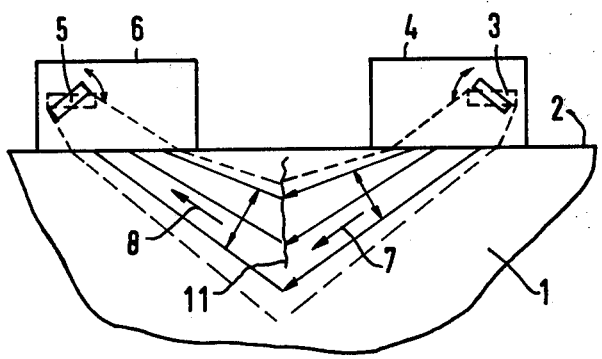
FIG. 3 shows two probes in which the incident and reflected angle of the wave beam can be adjusted.
Figure 4:
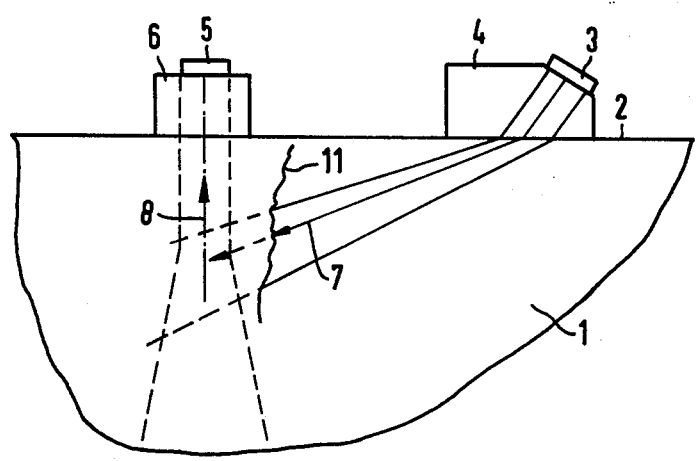
FIG. 4 shows an arrangement in which a probe for longitudinal waves operates as transmitter and a compressional wave probe as receiver.

FIG. 3, probes 4 and 6 have no fixed oscillators, but are arranged to be turned so as to permit the angle of incidence and reflection of the sound beam to be changed. As a result, the point of intersection of beams 7 and 8 may move along the entire extension of the defect until probe 6 receives a clear scatter signal from the bottom end of the defect. By automatic recording of the relationship between the scatter signal received and the angle is it possible to use the artificial defects for exact determination of the depth following calibration similar to that in the arrangement of FIG. 1. In FIG. 4, a compressional wave probe is used which is capable of receiving a longitudinal wave beam propagated normal to the surface, instead of the receiving angle probe 6. In the case shown in FIG. 4, crack 11 completely shades the exciting wave beam 7, so that the compressional wave probe 6 will hardly receive any scatter signals.

In FIG. 5, the necessary movement of both probes 4 and 6 in FIG. 1 is replaced by fixed or stationary probes 4 and 6 which carry several oscillators on a suitably shaped plastic support. The transmitting oscillators 3, 3A, 3B, 3C and the receiving oscillators 5, 5A, 5B, 5C are cemented in position at an angle to ensure that longitudinal wave beams are emitted and received (7 and 8, respectively). The angles of incidence can be adjusted to suit the geometrical configuration of the application involved. In actual operation, the oscillators 3 and 5, 3A/5A, 3C/5C of this probe are successively switched on with an ultrasonic pulse-echo device, working as transmitters and receivers. With each individual oscillator suitably focussed onto the intersection area at defect 11, structural scatter signals of any intensity are only received when the intersection point is at the bottom end of the defect (in the case shown, located by 3C and 5C). This arrangement may also be adjusted by means of artificial or simulated defects in test blocks. The following procedure provides a further simple means for adjustment: in the case of the probe positioned on the defect-free surface of a workpiece, all oscillator combinations 3/5, 3A/5A, 3B/5B, 3C/5C are successively switched on and the scatter signal set at the same height for each combination, which may be done by varying the transmitting power or the sensitivity of the receiving probe. If there is a clear change in the height of the scatter signal when switching from oscillators 3B/5B to 3C/5C, this indicates that the lowermost tip of the defect is located between the points of intersection of the wave beams of combination 3B/5B and 3C/5C.

The arrangements shown in FIGS. 1–5 may be varied in a number of ways. For example, the oscillators may be of different shape (narrow rectangles as oscillators with cylindrical lenses placed in front to achieve a suitable focus area, and the like), but all these possible variations have the objective of utilizing the structural scatter in order to obtain information as to whether the point of intersection of two imaginary wave beams is in the area to which the tip of the defect extends or below it.

We claim:

1. A method of determining depth propagation of a defect in a body by ultrasonic materials testing wherein a first angle probe having an ultrasonic wave transmitting oscillator produces a scatter signal at structural inhomogeneities of a body formed with a defect and the scatter signal is received by an ultrasonic wave receiving oscillator of a second angle probe, which comprises: transmitting an ultrasonic wave at a first angle along a first line in direction towards the defect so that the scatter signal there at is shadowed by the defect and diminished in intensity; receiving the diminished signal from the defect at a second angle in a direction along a second line intersecting with the first line at the defect, transmitting additional ultrasonic waves and receiving diminished scatter signals along respective lines intersecting at the defect at varying depths of the body and ascertaining the depth propagation of the defect by a marked increase in intensity of the received signal when the intersection of the respective lines along which the ultrasonic wave is transmitted and the scatter signal is received reach beyond the innermost limit of the defect.

2. A method as set forth in claim 1 which further comprises using the first longitudinal wave of the waves scattered within the body for determining properties thereof at various depths therein by means of a frequency-and correlation analysis of the received scatter signal.

3. A method as set forth in claim 1 wherein the relationship of the signal amplitude to the location of the point of intersection of two imaginary ultrasonic waves is determined by means of an artificial defect in calibration tests, and further comprises: simulating an artificial defect in a model; calibrating the dependence of the received and scattered signal on the intersection location of the ultrasonic waves by the simulated defect in the model to obtain a calibration curve; and exactly determining the depth propagation of the simulated defect in the structure from the calibration curve, from the intersection location and from the signal amplitude of the received and scattered signal.

4. A method according to claim 1 wherein the selective displacement of the respective angle probe means includes selectively displacing and rotating said probe means.

* * * * *